United States Patent [19]

Kellogg

[11] Patent Number: 4,582,829

[45] Date of Patent: Apr. 15, 1986

[54] ANTIBACTERIAL 6'-(2-AMINO-2-[4-ACYLOXYPHENYL-]ACETAMIDO)PENICILLANOYLOX-YMETHYL PENICILLANATE 1,1-DIOXIDE COMPOUNDS

[75] Inventor: Michael S. Kellogg, Waterford, Conn.

[73] Assignee: Pfizer Inc., New York, N.Y.

[21] Appl. No.: 734,504

[22] Filed: May 15, 1985

Related U.S. Application Data

[60] Division of Ser. No. 407,540, Aug. 12, 1982, Pat. No. 4,540,687, which is a continuation-in-part of Ser. No. 300,421, Sep. 9, 1981, abandoned.

[51] Int. Cl.$^4$ .................. A61K 31/43; C07D 499/32
[52] U.S. Cl. .................. 514/193; 260/239.1
[58] Field of Search .................. 260/239.1; 514/193

[56] References Cited

U.S. PATENT DOCUMENTS

| | | | |
|---|---|---|---|
| 2,985,648 | 5/1961 | Doyle et al. | 260/239.1 |
| 3,520,876 | 7/1970 | Alburn et al. | 260/239.1 |
| 3,869,449 | 3/1975 | Godtfredsen | 260/239.1 |
| 4,053,360 | 10/1977 | Bouzard et al. | 260/239.1 X |
| 4,234,579 | 11/1980 | Barth | 514/200 |
| 4,244,951 | 1/1981 | Bigham | 514/193 |
| 4,309,347 | 1/1982 | Bigham | 260/245.2 R |

FOREIGN PATENT DOCUMENTS

| | | |
|---|---|---|
| 881675 | 8/1980 | Belgium . |
| 2044255 | 10/1980 | United Kingdom . |

Primary Examiner—Natalie Trousof
Assistant Examiner—Vera C. Clarke
Attorney, Agent, or Firm—Charles J. Knuth; Peter C. Richardson; Mark Dryer

[57] ABSTRACT 6-(2-Amino-2-[4-acyloxyphenyl]acetamido)penicillanoyloxymethyl esters of penicillanic acid 1,1-dioxide are useful as antibacterial agents. Derivatives of the aforesaid antibacterial agents which have an amino protecting group on the amino function in the 2-amino-2-(4-acyloxyphenyl)acetamido side chain are useful intermediates to the antibacterial agents themselves.

8 Claims, No Drawings

ANTIBACTERIAL 6'-(2-AMINO-2-[4-ACYLOXYPHENYL]ACETAMIDO)PENICILLANOYLOXYMETHYL PENICILLANATE 1,1-DIOXIDE COMPOUNDS

CROSS-REFERENCE TO RELATED APPLICATIONS

This is a division of application Ser. No. 407,540, filed on Aug. 12, 1982, now U.S. Pat. No. 4,540,687, which application is a continuation-in-part of application Ser. No. 300,421, filed Sept. 9, 1981 now abandoned.

BACKGROUND OF THE INVENTION

This invention relates to new chemical compounds which are of value as antibacterial agents. More particularly it relates to certain new bis-esters of methanediol, in which one hydroxy group of the methanediol has been esterified with the carboxy group of a 6-(2-amino-2-[4-acyloxyphenyl]acetamido)penicillanic acid compound and the other hydroxy group has been esterified with the carboxy group of a beta-lactamase inhibitor. Said latter beta-lactamase inhibitor is one of the type which contains a beta-lactam ring as well as a carboxy group.

U.S. Pat. No. 4,244,951, Belgian Pat. No. 887,173 and published British patent application No. 2,044,255 disclose a variety of bis-esters of methanediol of the formula

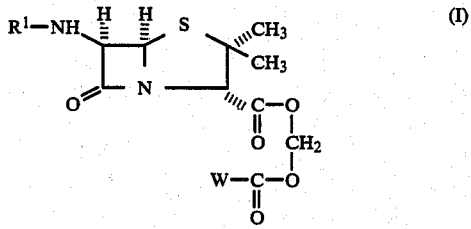

and the pharmaceutically-acceptable salts thereof, wherein $R^1$ represents certain acyl groups and the radical W—C(=O)—O— represents a radical of a betalactamase inhibitor, W—C(=O)—OH, which contains a beta-lactam ring as well as a carboxy group, said compounds of formula I being useful as antibacterial agents. In particular, $R^1$ can represent a 2-amino-2-(4-hydroxyphenyl)acetyl group. However, it has now been found that compounds of the formula I, wherein the group $R^1$ represents certain 2-amino-2-[4-acyloxyphenyl]acetyl groups, constitute a new genus of bis-esters of methanediol, having outstanding value in the treatment of bacterial infections in mammals. Additionally, compounds of formula I, in which $R^1$ represents certain 2-(protected amino)-2-(4-acyloxyphenyl)acetyl groups, are useful as intermediates to the antibacterial agents of this invention.

The antibacterial agents of the present invention are efficiently absorbed from the gastrointestinal tract of mammals, and after absorption they are transformed into 6-(2-amino-2-[4-hydroxyphenyl]acetamido)penicillanic acid (amoxicillin) and a betalactamase inhibitor.

6-(2-Amino-2-[4-hydroxyphenyl]acetamido)penicillanic acid and 6-(2-amino-2-[4-acyloxyphenyl]acetamido)penicillanic acids are known; see further U.S. Pat. Nos. 2,985,648, 3,520,876 and 4,053,360. Penicillanic acid 1,1-dioxide is known from U.S. Pat. No. 4,234,579.

SUMMARY OF THE INVENTION

In its broadest sense, this invention provides new antibacterial agents of the formula

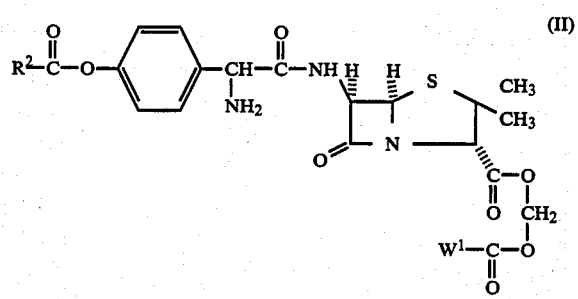

the pharmaceutically acceptable acid addition salts thereof and the pharmaceutically-acceptable base salts thereof;

wherein $R^2$ is selected from the group consisting of alkyl having from one to six carbons, alkoxy having from one to six carbons, HOOC—$(CH_2)_n$—, HOOC—$C(CH_3)_2$—, 3-carboxycyclopentyl, 4-carboxycyclohexyl, $R^8R^9N$— and a group of the formula

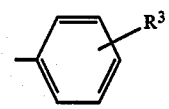

wherein n is an integer from 0 to 6; $R^8$ and $R^9$ are each selected from the group consisting of hydrogen, alkyl having from one to six carbons, phenyl and phenyl substituted with fluoro, chloro, bromo, iodo, alkyl having from one to four carbons or alkoxy having from one to four carbons, provided that $R^8$ and $R^9$ are not both hydrogen; and $R^3$ is selected from the group consisting of hydrogen, alkyl having one to four carbons, alkoxy having one to four carbons, fluoro, chloro, bromo, iodo and cyano;

and the radical $W^1$—C(=O)—O— represents a radical of a beta-lactamase inhibitor, $W^1$—C(=O)—OH, which contains a beta-lactam ring as well as a carboxy group.

Typical examples of the beta-lactamase inhibitor radicals, $W^1$—C(=O)—O—, are

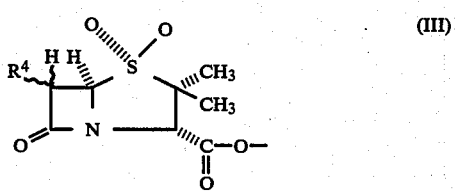

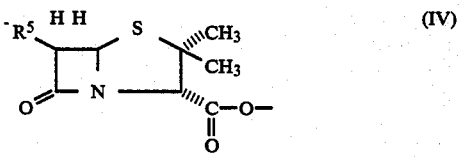

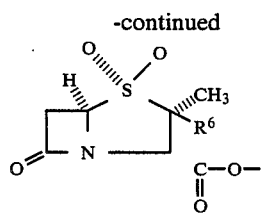

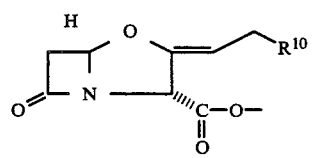

wherein R⁴ is selected from the group consisting of hydrogen and hydroxymethyl;

R⁵ is selected from the group consisting of chloro, bromo and iodo;

R⁶ is selected from the group consisting of -CH₂—Cl, —CH₂—O—CO—CH₃ and —C(=O)—OR¹¹, wherein R¹¹ is alkyl having from one to four carbons;

and R¹⁰ is selected from the group consisting of hydroxy and those radicals known to impart beta-lactamase inhibiting activity to clavulanic acid when attached to the corresponding position in clavulanic acid.

However, the preferred antibacterial agents of this invention are the compounds of formula II, wherein W¹—C(=O)—O— is of formula III and R⁴ is hydrogen. Within this preferred group, especially preferred compounds are those wherein R² is said alkyl. An especially preferred individual compound of the invention is the compound of formula II, wherein W¹—C(=O)—O— is of formula III and R⁴ is hydrogen, and R² is propyl.

This invention also provides compounds of the formula

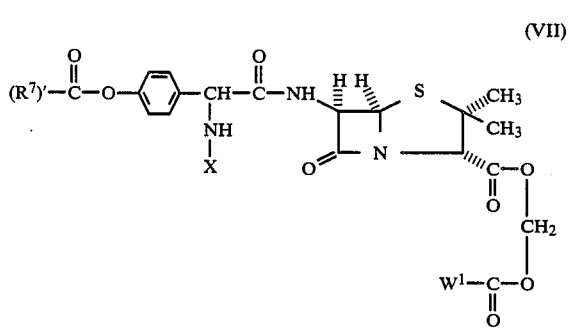

wherein W¹—C(=O)—O— is as defined previously, (R⁷)' is the group R² but with any free carboxy group therein protected and X represents certain amino protecting groups. Said compounds of formula VII are useful as intermediates to said compounds of formula II.

In the compounds of formula VII, when W¹—C(=O)—O— is the formula III, wherein R⁴ is hydrogen, groups which are used for X are 1-methyl-2-alkoxycarbonylvinyl groups, benzyloxycarbonyl and 4-nitrobenzyloxycarbonyl. Especially preferred is 1-methyl-2-methoxycarbonylvinyl.

DETAILED DESCRIPTION OF THE INVENTION

This invention relates to derivatives of penicillanic acid, which is represented by the following structural formula

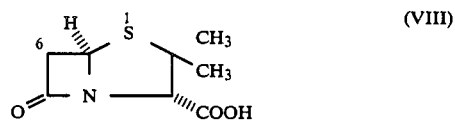

In formula VIII, broken line attachment of a substituent to the bicyclic nucleus indicates that the substituent is below the plane of the bicyclic nucleus, and such a substituent is said to be in the alpha-configuration. Conversely, solid line attachment of a substituent to the bicyclic nucleus indicates that the substituent is attached above the plane of the nucleus, and this latter configuration is referred to as the beta-configuration. Additionally, wavy line attachment of a substituent to the bicyclic nucleus indicates that the substituent is in the alpha-configuration or the beta-configuration or that a mixture is present.

Thus, for example, using this system, the compounds of formulae II and VII, wherein W¹—C(=O)—O— is of the formula III and R⁴ is hydrogen, are named as derivatives of penicillanoyloxymethyl penicillanate (IX), in which primed and unprimed locants are used to distinguish between the two ring systems, viz:

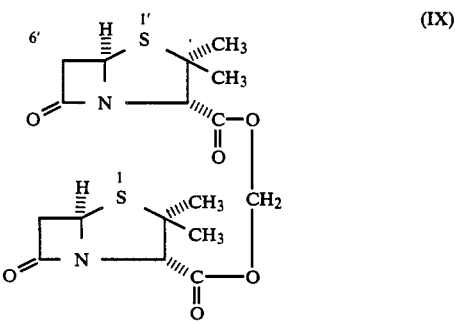

Additionally, throughout this specification, whenever reference is made to a compound which has a 2-amino-2-(substituted)acetamido or 2-(substituted amino)-2-(substituted)acetamido group at the 6-position of a penicillanic acid derivative, it is to be understood that this refers to a compound in which said 2-amino-2-(substituted)acetamido or 2-(substituted amino)-2-(substituted)acetamido has the D-configuration.

The compounds of formula II, wherein R² is as defined previously, and W¹—C(=O)—O— is either of the formula III wherein R⁴ is hydrogen, the formula IV or the formula V, can be prepared as follows. The phenolic hydroxy group in the appropriate compound of the formula

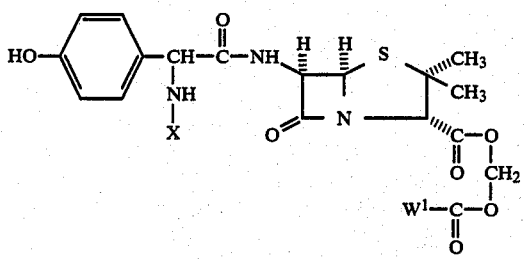

wherein X is an amino protecting group, is acylated with either: (i) an activated derivative of a carboxylic acid of the formula $R^7$—C(=O)—OH, wherein $R^7$ is the group $R^2$, other than $R^8R^9N$—, and with any free carboxy groups therein protected; (ii) a carbamoyl chloride of the formula $R^8R^9N$—C(=O)—Cl, provided that neither $R^8$ nor $R^9$ is hydrogen; or (iii) an isocyanate of the formula $R^8$—N=C=O, to give the corresponding compound of the formula

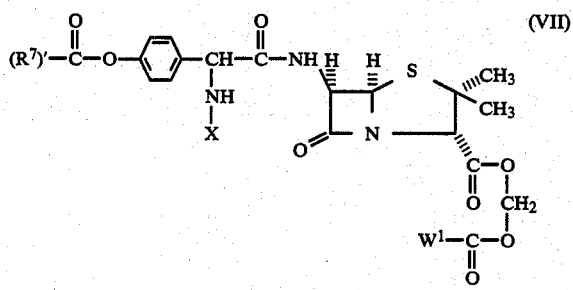

wherein $(R^7)'$ is $R^7$ or $R^8R^9N$— and $W^1$—C(=O)—O— is as defined previously. This acylation is followed by removal of the protecting group X, and, if necessary, removal of any protecting group in $(R^7)'$.

A variety of protecting groups can be used for the group X. However, the group X must be compatible with the group $W^1$—C(=O)—O—. The group X must be removable using conditions which do not adversely affect the group $W^1$—C(=O). Thus when $W^1$—C(=O)—O— is of formula III, wherein $R^4$ is hydrogen, convenient groups for X are 1-methyl-2-alkoxycarbonylvinyl groups having 1 to 3 carbons in said alkoxy moiety, the benzyloxycarbonyl group and the 4-nitrobenzyloxycarbonyl group. 1-Methyl-2-methoxycarbonylvinyl(—C[CH_3]=CH—COOCH_3) is particularly preferred.

The acylation of a compound of formula X can be carried out by reacting said compound of formula X with an acid chloride of the formula $R^7$—CO—Cl, an acid anhydride of the formula $(R^7—CO)_2O$, said carbamoyl chloride of the formula $R^8R^9N$—C(=O)—Cl or said isocyanate of the formula $R^8$—N=C=O. The acylation reaction is usually conducted in a reaction-inert solvent system. In a typical procedure, from 0.5 to 2.0 molar equivalents, and preferably about 1 molar equivalent, of the acylating agent of formula $R^7$—CO—Cl, $(R^7—CO)_2O$, $R^8R^9N$—C(=O)—Cl or $R^8$—N=C=O is contacted with said compound of formula X, in a reaction-inert solvent, in the presence of a tertiary amine, at a temperature in the range from $-10°$ to $30°$ C. Reaction-inert solvents which can be used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone; tertiary amides, such as N,N-dimethylformamide and N-methylpyrrolidone; acetonitrile; and mixtures thereof. The tertiary amine is normally used in an amount equivalent to the compound of formula $R^2$—CO—Cl, $(R^2—CO)_2O$, $R^8R^9N$—C(=O)—Cl or $R^8$—N=C=O, and typical tertiary amines which can be used are triethylamine, tributylamine, diisopropylethylamine, pyridine and 4-dimethylaminopyridine.

The compounds of formula VII can be isolated by conventional means, such as removal of the solvent by evaporation. They can be purified, if desired, by conventional methods such as recrystallization or chromatography; alternatively, the protecting group X can be removed from the crude acylation product.

The protecting group X is removed from a compound of formula VII by a conventional method for that particular protecting group, but due regard must be given to the lability of the beta-lactam rings and the methylenedioxy linkage.

The 1-methyl-2-alkoxycarbonylvinyl groups can be removed simply by exposing the compound of formula VII to an aqueous or partially aqueous solvent system at an acidic pH, i.e. a pH from 0.5 to 3. This is conveniently achieved by treating the acylation product with water and one molar equivalent of a strong acid, at room temperature, optionally in the presence of a co-solvent. Typical examples of strong acids which can be used are hydrochloric acid, hydrobromic acid, perchloric acid, sulfuric acid, nitric acid and sulfonic acids, such as methanesulfonic acid, benzenesulfonic acid, toluenesulfonic acids and naphthalenesulfonic acids. A variety of co-solvents can be used, the major requirements of such a solvent being that it is at least partially miscible with water and it does not adversely affect either the starting material or the product. Typical co-solvents are low molecular weight ketones, such as acetone and low molecular weight ethers, such as tetrahydrofuran and 1,2-dimethoxyethane. The reaction is usually complete within an hour, and the product is isolated by conventional methods. In many instances, it is sufficient simply to remove the co-solvent by evaporation in vacuo, remove the alkyl acetoacetate by extraction with a water-immiscible solvent such as diethyl ether, and then lyophilize the remaining aqueous solution. This affords the requisite compound of formula II as a salt corresponding to the acid which has been added initially.

The benzyloxycarbonyl and 4-nitrobenzyloxycarbonyl groups can be removed from a compound of formula VII by catalytic hydrogenolysis. In this case, a compound of formula VII, wherein X is benzyloxycarbonyl or 4-nitrobenzyloxycarbonyl, is stirred or shaken under an atmosphere of hydrogen, or hydrogen mixed with an inert diluent such as nitrogen or argon, in the presence of a catalytic amount of a hydrogenolysis catalyst. Convenient solvents for this hydrogenolysis are lower-alkanols, such as methanol and isopropanol; ethers, such as tetrahydrofuran and dioxan; low molecular weight esters, such as ethyl acetate and butyl acetate; chlorinated hydrocarbons, such as dichloromethane and chloroform; water; and mixtures of these solvents. However, it is usual to choose conditions under which the starting material is soluble. The hydrogenolysis is usually carried out at a temperature in the range from 0 to 60° C. and at a pressure in the range from 20 to 100 psig, preferably about 50 psig. The catalysts used in this hydrogenolysis reaction are the type of agents known in the art for this kind of transformation, and typical examples are the noble metals, such as nickel, palladium, platinum and rhodium. It is often convenient to suspend the catalyst on an inert support; a particularly convenient catalyst is palladium suspended on an inert support such as carbon, e.g. 10% palladium on carbon. When 10% palladium on carbon is used, it is usually used in a weight amount that is 0.5 to 5.0, and preferably about 1.0, times the weight of the compound of formula VII.

As indicated hereinbefore, when it is desired to prepare a compound of formula II in which the group $R^2$ possesses a carboxy group, e.g. $R^2$ is $HOOC-(CH_2)_n-$, it is advantageous to protect said carboxy group during the acylation of the compound of formula X. Convenient groups for achieving this carboxy protection are the benzyl group and the 4-nitrobenzyl group. Accordingly, when it is desired to prepare a compound of formula II in which $R^2$ possesses a carboxy group, it is necessary to remove the carboxy protecting group from the compound of formula VII as well as the protecting group X. As will be appreciated by one skilled in the art, when X is benzyloxycarbonyl or 4-nitrobenzyloxycarbonyl, and it is removed by catalytic hydrogenolysis as described previously, the benzyl or 4-nitrobenzyl carboxy protecting groups are removed concomitantly. However, if a non-hydrogenolytic method is used to remove the protecting group X, the benzyl or 4-nitrobenzyl protecting groups must be removed in a separate step. In this case they are conveniently removed by hydrogenolysis, using the method described for removal of X as benzyloxycarbonyl or 4-nitrobenzyloxycarbonyl.

The compounds of formula II, wherein R2 is as defined previously, and $W^1-C(=O)-O-$ is of formula III wherein $R^4$ is hydroxymethyl, or of formula VI, can be prepared as follows. Firstly, the compound of the formula

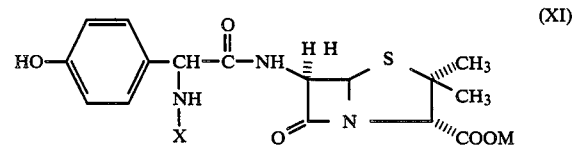

(XI)

is acylated with an activated derivative of a carboxylic acid of the formula $R^7-C(=O)-OH$, a carbamoyl chloride of the formula $R^8R^9N-C(=O)-Cl$ or an isocyanate of the formula $R^8N=C=O$, wherein M is a carboxylate salt forming cation, X is an amino protecting group of the type mentioned earlier and $R^7$, $R^8$ and $R^9$ are as defined previously, to give a compound of the formula

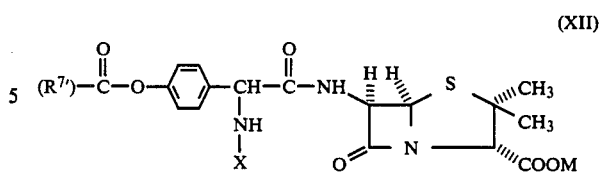

(XII)

wherein $(R^7)'$ is $R^7$ or $R^8R^9N-$.

This acylation is carried out in the same manner as described earlier for the acylation of a compound of the formula X with an activated derivative of a carboxylic acid of the formula $R^7-C(=O)-OH$, a carbamoyl chloride of the formula $R^8R^9N-C(=O)-Cl$ or an isocyanate of the formula $R^8N=C=O$. Examples for M are sodium, potassium and tetra-n-butylammonium.

Secondly, the compound of the formula XII is converted into an ester of the formula

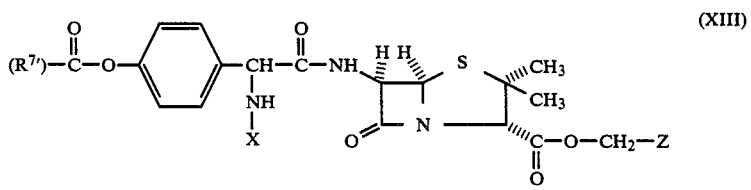

(XIII)

wherein Z is a good leaving group, e.g. chloro, bromo or iodo. This is carried out in conventional fashion for this kind of transformation. See, for example, U.S. Pat. Nos. 3,850,908 and 4,244,951, published British patent application No. 2,044,255, published Dutch patent application No. 81/00209 and Belgian Pat. No. 887,173.

Thirdly, the compound of formula XIII is coupled with the appropriate compound of the formula $W^1-C(=O)-OM$, wherein $W^1$ and M are as previously indicated. This affords a compound of the formula VII, which is then converted into a compound of formula II by removal of the amino protecting group X, and, if necessary, any carboxy protecting group in $(R^7)'$, by the methods previously described.

The compounds of the formula II will form acid addition salts, and these acid addition salts are considered to be within the scope and purview of this invention. Said acid addition salts are prepared by standard methods for penicillin compounds, for example by combining a solution of the compound of formula II in a suitable solvent (e.g. water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate, benzenesulfonate, 4-toluenesulfonate and 2-naphthalenesulfonate salts.

Those compounds of the formula II which have a carboxy group in the group $R^2$ will form base salts, and these base salts are considered to be within the scope and purview of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]-non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of the formula II, and the salts thereof, can be purified by conventional methods for penicillin compounds, e.g. recrystallization or chromatography, but due regard must be given to the lability of the beta-lactam ring systems and the methylenedioxy linkage.

Those compounds of formula X which are known are prepared by the known method, and those compounds of formula X which are analogs of known compounds are prepared by methods which are analogous to the known methods. In general, a compound of the formula X is prepared by reaction of a compound of the formula

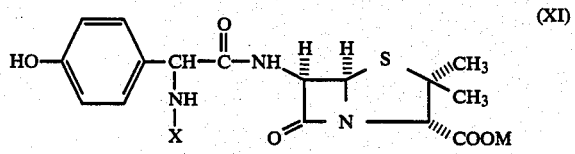

(XI)

wherein X is an amino protecting group and M is a carboxylate salt forming cation, with the appropriate compound of the formula $W^1$—C(=O)—O—$CH_2$—Z, wherein Z is a good leaving group, e.g. chloro, bromo or iodo. Examples of M are sodium, potassium and tetra-n-butylammonium. See further, U.S. Pat. No. 4,244,951, published British patent application No. 2,044,255, published Dutch patent application No. 81/00209 and Belgian Pat. No. 887,173.

Methods for the preparation of the compounds of the formula XI are taught in U.S. Pat. Nos. 4,244,951 and 3,325,479.

Some of the compounds of the formula $W^1$—C(=O)—O—$CH_2$—Z are known compounds and the remainder are analogs of known compounds. Those compounds which are known are prepared by the published procedures, and those compounds which are analogs of known compounds are prepared by methods analogous to the published procedures. In general a salt of the corresponding free acid, $W^1$—C(=O)—OH, is reacted with a compound of the formula Z—$CH_2$—$Z^1$ and it is the same as, or a better leaving group than, Z. See further, for example, U.S. Pat. No. 4,244,951, published British patent application No. 2,044,255, published Dutch patent application No. 81/00209 and Belgian Pat. No. 887,173.

For the preparation of the compounds of the formula $W^1$—C(=O)—OH and their salts, see for example, U.S. Pat. Nos. 4,234,579, 4,287,181, 4,256,733 and 4,110,165; published Dutch patent application No. 81/00209; Belgian Pat. No. 887,173; and published European patent application No. 13,517.

The compounds of formula II possess in vivo antibacterial activity in mammals, and this activity can be demonstrated by standard techniques for penicillin compounds. For example, the compound of formula II is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula II. The compounds of formula II can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

A compound of formula II breaks down to 6-(2-amino-2-[4-hydroxyphenyl]acetamido)penicillanic acid (amoxicillin) and a compound of formula $W^1$—C(=O)—OH, e.g. penicillanic acid 1,1-dioxide (sulbactam), after administration to a mammalian subject by both the oral and parenteral route. The compound of formula $W^1$—C(=O)—OH then functions as a beta-lactamase inhibitor, and it increases the antibacterial effectiveness of the amoxicillin. Thus the compounds of the formula II will find use in the control of bacteria which are susceptible to a 1:1 mixture of amoxicillin and a compound of formula $W^1$—C(=O)—OH, e.g. susceptible strains of Escherichia coli and Staphylococcus aureus.

In determining whether a particular strain of Escherichia coli or Staphylococcus aureus is sensitive to a particular compound of formula II, the in vivo test described earlier can be used. Alternatively, the minimum inhibitory concentration (MIC) of a 1:1 mixture of amoxicillin and a compound of formula $W^1$—C(=O)—OH can be measured. The MIC's can be measured by the procedure recommended by the International Collaborative Study on Antibiotic Sensitivity Testing (Ericcson and Sherris, Acta. Pathologica et Microbiologia Scandinav, Supp. 217, Section B: 64–68[1971]), which employs brain heart infusion (BHI) agar and the inocula replicating device. Overnight growth tubes are diluted 100 fold for use as the standard inoculum [20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Nuclear magnetic resonance spectra (NMR) were measured for solutions in deuterated chloroform ($CDCl_3$) or deuterated dimethyl sulfoxide ($DMSO-d_6$), and peak positions are reported in parts per million downfield from tetramethylsilane. The following abbreviations for peak shapes are used: bs, broad singlet; s, singlet; d, doublet; t, triplet; q, quartet; m, multiplet.

EXAMPLE 1

6'-(2-Amino-2-[4-isobutyryloxyphenyl]acetamido)-penicillanoyloxymethyl Penicillanate 1,1-Dioxide Hydrochloride To a stirred solution of 1.5 g of 6'-(2-[1-methyl-2-methoxycarbonylvinylamino]-2-[4-isobutyryloxyphenyl]acetamido)penicillanoyloxymethyl penicillanate 1,1-dioxide in 30 ml of acetone was added 20 ml of 0.1 N hydrochloric acid. Stirring was continued for 5 minutes and then the acetone was removed by evaporation *in vacuo*. The remaining aqueous solution was extracted twice with 30 ml portions of diethyl ether. The extracts were discarded, and the aqueous layer was filtered through Celite (a diatomaceous silica product). The filtrate was lyophilized to give 1.09 g of the title compound as a solid.

The NMR spectrum of the product (in $DMSO-d_6$) showed absorptions at 1.20–1.60 (m, 18H), 2.64–3.00 (m, 1H), 3.05–3.92 (m, 2H), 4.40 (s, 1H), 4.50 (s, 1H), 5.05–5.30 (m, 2H), 5.32–5.60 (m, 2H), 5.85 (s, 2H), 7.10 (d, 2H) and 7.50 (d, 2H) ppm.

EXAMPLE 2

Hydrolysis of the products of Examples 7, 9, 11 and 13 with 0.1 N hydrochloric acid, substantially according to the procedure of Example 1, afforded the following compounds

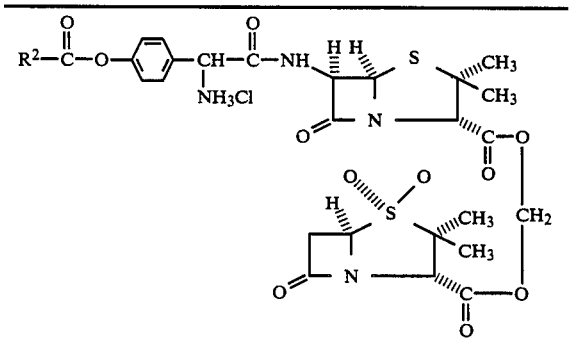

| $R^2$ | Yield (%) | NMR; $DMSO-d_6$; ppm |
|---|---|---|
| methyl | 75 | 1.20–1.64 (m, 12H), 2.28 (s, 3H) 3.00–3.90 (m, 2H), 4.43 (s, 1H), 4.50 (s, 1H), 5.03–5.30 (m, 2H), 5.30–5.60 (m, 2H), 5.90 (s, 2H), 7.18 (d, 2H) and 7.55 (d, 2H) |
| ethyl | 71 | 1.19 (t, 3H) 1.42 (s, 6H), 1.52 (s, 6H), 2.62 (q, 2H), 3.08–3.92 (m, 2H) 4.42 (s, 1H), 5.52 (s, 1H), 5.08–5.18 (m, 2H), 5.35–5.60 (m, 2H), 5.89 (s, 2H), 7.15 (d, 2H), 7.52 (d, 2H) |
| t-butyl | 83 | 1.15–1.60 (m, 21H), 3.05–3.94 (m, 2H), 4.48 (s, 1H), 4.55 (s, 1H), 5.05–5.30 (m, 2H), 5.40–5.70 (m, 2H), 5.92 (s, 2H), 7.18 (d, 2H), 7.60 (d, 2H), 8.60–9.30 (bs, 3H), 9.50 (s, 1H) |
| t-butylmethyl | 82 | 1.08 (s, 9H), 1.38 (s, 6H), 1.44 (s, 6H), 2.44 (s, 2H), 3.00–3.90 (m, 2H), 4.40 (s, 1H), 4.52 (s, 1H), 5.05–5.30 (m, 2H), 5.32–5.60 (m, 2H), 5.88 (bs, 2H), 7.10 (d, 2H), 7.58 (d, 2H) |

-continued

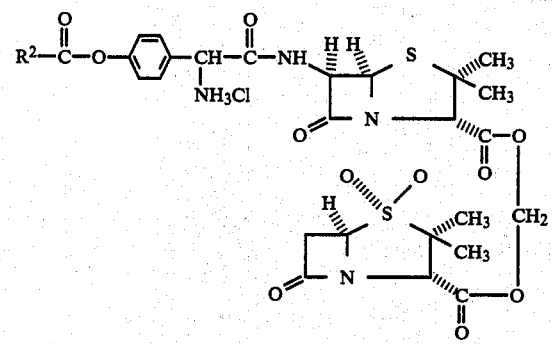

| R² | Yield (%) | NMR; DMSO-d₆; ppm |
|---|---|---|
| ethoxy | 36 | 1.22–1.60 (m, 15H), 3.02–3.90 (m, 2H), 4.24 (q, 2H), 4.42 (s, 1H), 4.52 (s, 1H), 5.00–5.30 (m, 2H), 5.35–5.60 (m, 2H), 5.86 (s, 2H), 7.22 (d, 2H), 7.55 (d, 2H) |
| isobutoxy | 67 | 0.90 (s, 3H), 1.04 (s, 3H), 1.25–1.5 (m, 12H), 1.60–1.20 (m, 1H), 3.04–3.88 (m, 2H), 4.00 (d, 2H), 4.45 (s, 1H), 4.54 (s, 1H), 5.00–5.28 (m, 2H), 5.30–5.60 (m, 2H), 5.90 (s, 2H), 7.24 (d, 2H), 7.62 (d, 2H) |
| phenyl | 49 | 1.30 (s, 6H), 1.52 (s, 6H), 3.00–3.82 (m, 2H), 4.30 (s, 1H), 4.40 (s, 3H), 5.00–5.25 (m, 2H), 5.25–5.60 (m, 2H), 5.90 (s, 2H), 7.20 (d, 2H), 7.38–7.64 (m, 5H), 7.9–8.1 (m, 2H) |
| 4-methoxyphenyl | 77 | 1.48 (s, 6H), 1.56 (s, 6H), 3.05–3.90 (m, 2H), 3.94 (s, 3H), 4.5 (s, 1H), 4.57 (s, 1H), 5.05–5.35 (m, 2H), 5.35–5.68 (m, 2H), 5.95 (s, 2H), 7.00–7.50 (m, 4H), 7.68 (d, 2H), 8.08 (d, 2H) |
| 4-cyanophenyl | 60 | 1.40 (s, 6H), 1.50 (s, 6H), 3.05–3.90 (m, 2H), 4.44 (s, 1H), 4.55 (s, 1H), 5.05–5.32 (m, 2H), 5.32–5.62 (m, 2H), 5.90 (s, 2H), 7.35 (d, 2H), 7.68 (d, 2H), 8.05 (d, 2H), 8.28 (d, 2H) |

EXAMPLE 3

By hydrolysis of the appropriate compound from Example 10 or Example 12 with 0.1 N hydrochloric acid, according to the procedure of Example 1, the following compounds can be prepared.

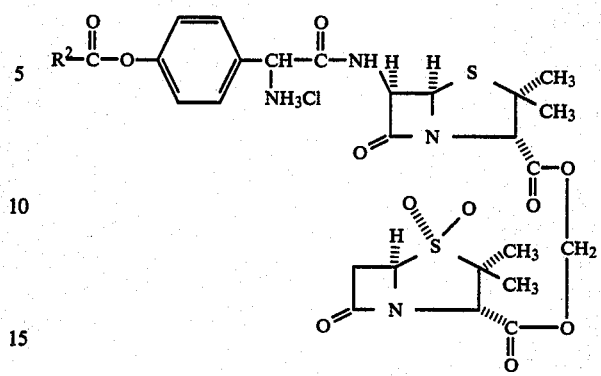

R²
hexyl
methoxy
hexyloxy
2-methylphenyl
3-butylphenyl
3-propoxyphenyl
4-(2-isobutoxy)phenyl
3-fluorophenyl
2-chlorophenyl
4-bromophenyl
3-iodophenyl
dimethylamino
ethylpropylamino
ethylhexylamino
N—methylanilino
diphenylamino
methyl(2-fluorophenyl)amino
phenyl(3-bromophenyl)amino
ethyl(4-methylphenyl)amino
isopropyl(3-butylphenyl)amino
di(4-methoxyphenyl)amino
di(3-butoxyphenyl)amino Additionally, hydrolysis of both 6'-(2-[1-methyl-2-ethoxycarbonylvinylamino]-2-[4-butyryloxyphenyl]acetamido)penicillanoyloxymethyl penicillanate 1,1-dioxide and 6'-(2-[1-methyl-2-isopropoxycarbonylvinylamino]-2-[4-butyryloxyphenyl]acetamido)penicillanoyloxymethyl penicillanate 1,1-dioxide according to the procedure of Example 1, affords 6'-(2-amino-2-[4-butyryloxyphenyl]acetamido)penicillanoyloxymethyl penicillanate 1,1-dioxide hydrochloride.

EXAMPLE 4

6'-(2-Amino-2-[4-acetoxyphenyl]acetamido)penicillanoyloxymethyl Penicillanate 1,1-Dioxide

A mixture of 1.9 g of 6'-(2-benzyloxycarbonylamino-2-[4-acetoxyphenyl]acetamido)penicillanoyloxymethyl penicillanate 1,1-dioxide, 50 ml of dichloromethane, 50 ml of isopropanol and 2.0 g of 10% palladium-on-carbon was shaken under an atmosphere of hydrogen at ca 45 psig for 20 minutes. At this point an additional 2.0 g of palladium-on-carbon was added and the mixture was shaken under hydrogen for 20 minutes at ca 45 psig. The procedure of adding an additional 2.0 g of palladium-on-carbon and shaking under hydrogen at ca 45 psig was then repeated four more times. The reaction mixture was then filtered through Celite (a diatomaceous silica product) and the residue filter cake) was washed well with 1:1 dichloromethaneisopropanol. The combined filtrate and washings were evaporated in vacuo to give a white solid, which was triturated under diethyl ether. This afforded 0.3 g of a first crop of the title compound.

The above filter cake was washed successively with 100 ml portions of acetone, dichloromethane and isopropanol. The combined washings were concentrated in vacuo to give a grey solid. The solid was triturated under diethyl ether. This afforded 0.2 g of a second crop of the title compound.

The NMR spectrum of the first crop of the title compound (in DMSO-$d_6$) showed absorptions at 1.35 (s, 6H), 1.48 (s, 6H), 2.28 (s, 3H), 3.00–3.90 (m, 2H), 4.42 (s, 1H), 4.50 (s, 1H), 5.00 (bs, 1H), 5.05–5.20 (m, 1H), 5.34–5.58 (m, 2H), 5.90 (s, 2H), 7.10 (d, 2H) and 7.54 (d, 2H) ppm.

EXAMPLE 5

6'-(2-Amino-2-[4-acetoxyphenyl]penicillanoyloxymethyl Penicillanate 1,1-Dioxide Hydrochloride The two crops of 6'-(2-amino-2-[4-acetoxyphenyl]acetamido)penicillanoyloxymethyl penicillanate 1,1-dioxide from Example 4 were combined and added to a cold (0° C.), stirred mixture which had been prepared from 20 ml of water and 6.7 ml of 0.1N hydrochloric acid. Stirring was continued for 15 minutes and then the mixture was filtered. The filtrate was lyophilized to give 0.34 g of the title salt.

EXAMPLE 6

6'-(2-Amino-2-[4-acetoxyphenyl]acetamido)penicillanoyloxymethyl Penicillanate 1,1-Dioxide Hydrogenolysis of 6'-(2-[4-nitrobenzyloxycarbonylamino]-2-[4-acetoxyphenyl]acetamido)penicillanoyloxymethyl penicillanate 1,1-dioxide according to the procedure of Example 4 affords the title compound.

EXAMPLE 7

6'-(2-[1-Methyl-2-methoxycarbonylvinylamino]-2-[4-acetoxyphenyl]acetamido)penicillanoyloxymethyl Penicillanate 1,1-Dioxide To a stirred solution of 3.5 g of 6'-(2-[1-methyl-2-methoxycarbonylvinylamino]-2-[4-hydroxyphenyl]acetamido)penicillanoyloxymethyl penicillanate 1,1-dioxide and 0.61 g of 4-dimethylaminopyridine in 30 ml of dichloromethane, was added 0.47 ml of acetic anhydride. Stirring was continued for 30 minutes, and then the reaction mixture was concentrated to half volume. The latter solution was then diluted with an equal volume of ethyl acetate and chromatographed on 100 g of silica gel using 1:1 ethyl acetate-dichloromethane as eluant. The appropriate fractions were combined and evaporated in vacuo to give 2.7 g of the title compound as a light orange foam.

EXAMPLE 8

6'-(2-[1-Methyl-2-methoxycarbonylvinylamino]-2-[4-isobutyryloxyphenyl]acetamido)penicillanoyloxymethyl Penicillanate 1,1-Dioxide To a stirred solution of 2.12 g of 6'-(2-[1-methyl-2-methoxycarbonylvinyl]-2-[4-hydroxyphenyl]acetamido)penicillanoyloxymethyl penicillanate 1,1-dioxide and 0.366 g of 4-dimethylaminopyridine in 30 ml of dichloromethane was added 0.314 ml of isobutyryl chloride. Stirring was continued for 30 minutes and then an additional 75 ml of dichloromethane was added. The mixture was washed successively with water and saturated sodium chloride solution, and then it was dried using sodium sulfate. The solvent was removed by evaporation in vacuo, and the residue was chromatographed on 150 g of silica gel, using 60:40 dichloromethane-ethyl acetate as eluant. This afforded 1.5 g of the title compound as a colorless foam.

EXAMPLE 9

6'-(2-[1-Methyl-2-methoxycarbonylvinylamino]-2[4-hydroxyphenyl]acetamido)penicillanoyloxymethyl penicillanate 1,1-dioxide was acylated with propionyl chloride, pivaloyl chloride, t-butylacetyl chloride, benzoyl chloride, 4-methoxybenzoyl chloride and 4-cyanobenzoyl chloride, respectively, substantially according to the procedure of Example 8. This afforded the following compounds

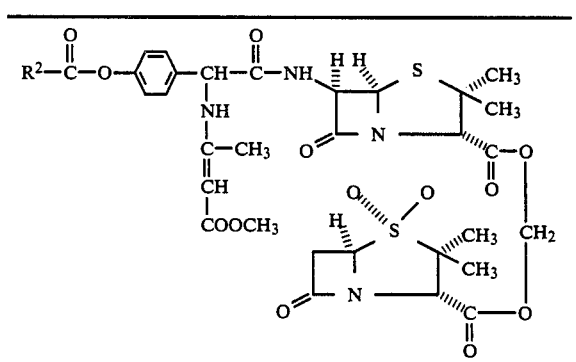

| $R^2$ | Yield (%) | NMR (in ppm) |
|---|---|---|
| ethyl | 52* | |
| t-butyl | 91 | 1.18–1.56 (m, 21H), 1.78 (s, 3H), 3.00–3.90 (m, 2H), 3.54 (s, 3H), 4.43 (s, 1H), 4.48 (s, 1H), 4.52 (s, 1H), 5.08–5.23 (m, 1H), 5.30–5.65 (m, 3H), 5.90 (s, 2H), 5.07 (d, 2H) and 7.40 (d, 2H) ppm (DMSO-$d_6$) |
| t-butylmethyl | 56 | 1.17 (s, 9H), 1.44 (s, 3H), 1.48 (s, 3H), 1.55 (s, 3H), 1.62 (s, 3H), 1.92 (s, 3H), 2.46 (s, 2H), 3.47 (d, 2H), 3.68 (s, 3H), 4.40 (s, 1H), 4.42 (s, 1H), 4.50–4.68 (m, 2H), 5.10 (d, 2H), 5.35–5.60 (m, 2H), 5.85 (s, 2H), 6.77 (d, 1H), 7.06 (d, 2H) and 7.40 (d, 2H) ppm (CDCl$_3$) |
| phenyl | 75 | 1.47 (s, 3H), 1.50 (s, 3H), 1.57 (s, 3H), 1.62 (s, 3H), 1.94 (s, 3H), 3.44 (d, 2H), 3.68 (s, 3H), 4.42 (s, 1H), 4.46 (s, 1H), 4.54–4.68 (m, 2H), 5.18 (d, 1H), 5.40–5.65 (m, 2H), 5.90 (s, 2H), 6.85 (d, 1H), 7.15–7.70 (m, 7H), 8.00–8.28 (m, 2H), 9.40 (d, 1H) (CDCl$_3$) |
| 4-methoxyphenyl | 79 | |
| 4-cyanophenyl | 96 | |

*This product was not chromatographed.

EXAMPLE 10

By acylation of 6'-(2-[1-methyl-2-methoxycarbonylvinylamino]-2-[4-hydroxyphenyl]acetamido)penicillanoyloxymethyl penicillanate 1,1-dioxide with the appropriate acid chloride of the formula $R^2$-CO-Cl, using the procedure of Example 8, the following compounds can be prepared.

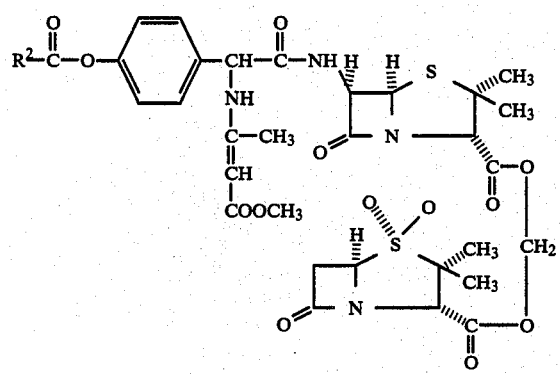

| R² |
|---|
| hexyl |
| 2-methylphenyl |
| 3-butylphenyl |
| 3-propoxyphenyl |
| 4-(2-isobutoxy)phenyl |
| 3-fluorophenyl |
| 2-chlorophenyl |
| 4-bromophenyl |
| 3-iodophenyl |
| dimethylamino |
| ethylpropylamino |
| ethylhexylamino |
| N—methylanilino |
| diphenylamino |
| methyl(2-fluorophenyl)amino |
| phenyl(3-bromophenyl)amino |
| ethyl(4-methylphenyl)amino |
| isopropyl(3-butylphenyl)amino |
| di(4-methoxyphenyl)amino |
| di(3-butoxyphenyl)amino |

Additionally, acylation of 6'-(2-[1-methyl-2-ethoxycarbonylvinylamino]-2-[4-hydroxyphenyl]acetamido)penicillanoyloxymethyl penicillanate 1,1-dioxide and 6'-(2-[1-methyl-2-isopropoxycarbonylvinylamino]-2-[4-hydroxyphenyl]acetamido)penicillanoyloxymethyl penicillanate 1,1-dioxide, respectively, with butyryl chloride, according to the procedure of Example 8, affords 6'(2-[1-methyl-2-ethoxycarbonylvinylamino]-2-[4-butyryloxyphenyl]-acetamido)penicillanoyloxymethyl penicillanate 1,1-dioxide and 6'-(2-[1-methyl-2-isopropoxycarbonylvinylamino]-2-[4-butyryloxyphenyl]acetamido)penicillanoyloxymethyl penicillanate 1,1-dioxide, respectively.

EXAMPLE 11

6'-(2-[1-Methyl-2-methoxycarbonylvinylamino]-2-[4-ethoxycarbonyloxyphenyl]acetamido)penicillanoyloxymethyl Penicillanate 1,1-Dioxide To a stirred solution of 2.12 g of 6'-(2-[1-methyl-2-methoxycarbonylvinylamino]-2-[4-hydroxyphenyl]acetamido)penicillanoyloxymethyl penicillanate 1,1-dioxide and 0.366 g of 4-dimethylaminopyridine in 30 ml of dichloromethane was added 0.28 ml of ethyl chloroformate. Stirring was continued for 45 minutes, and then the reaction mixture was diluted to 100 ml with dichloromethane. The resulting mixture was washed with water, followed by saturated sodium chloride solution, dried (Na₂SO₄) and evaporated in vacuo. This afforded 2.1 g of a foam. The foam was redissolved in 50 ml of dichloromethane and 0.52 ml of diisopropylethylamine, followed by 0.28 ml of ethyl chloroformate, was added. After ca. 10 minutes, the solvent was removed by evaporation in vacuo and the residue was dissolved in ethyl acetate. The ethyl acetate solution was washed successively with water, 0.05N hydrochloric acid, water and saturated sodium chloride. The dried (Na₂SO₄) solution was then evaporated in vacuo to give 2.0 g of the title compound as a foam.

EXAMPLE 12

By acylation of 6'-(2-[1-methyl-2-methoxycarbonylvinylamino]-2-[4-hydroxyphenyl]acetamido)penicillanoyloxymethyl penicillanate 1,1-dioxide with methyl chloroformate and hexyl chloroformate, respectively, the following compounds can be prepared:

6'-(2-[1-methyl-2-methoxycarbonylvinylamino]-2-[4-methoxycarbonyloxyphenyl]acetamido)penicillanoyloxymethyl penicillanate 1,1-dioxide and 6'-(2-[1-methyl-2-methoxycarbonylvinylamino]-2-[4-hexyloxycarbonyloxyphenyl]acetamido)penicillanoyloxymethyl penicillanate 1,1-dioxide, respectively.

EXAMPLE 13

6'-(2-[1-Methyl-2-methoxycarbonylvinylamino]2-[4-isobutoxycarbonyloxyphenyl]acetamido)penicillanoyloxymethyl Penicillanate 1,1-Dioxide To a stirred solution of 2.12 g of 6'-(2-[1-methyl-2-methoxycarbonylvinylamino]-2-[4-hydroxyphenyl]acetamido)penicillanoyloxymethyl penicillanate 1,1-dioxide and 0.52 ml of diisopropylethylamine in 30 ml of dichloromethane was added 0.388 ml of isobutyl chloroformate. Stirring was continued for 10 minutes and then ca. 20 mg of 4-dimethylaminopyridine was added. Stirring was continued for 30 minutes and then the solvent was removed by evaporation in vacuo. The residue was dissolved in ethyl acetate, and the solution was washed with water, followed by saturated sodium chloride solution. The solution was dried (Na₂SO₄) and evaporated in vacuo to give 2.2 g of a foam. The foam was purified by chromatography on 75 g of silica gel, using 60:40 dichloromethane-ethyl acetate as eluant. This afforded 1.4 g of the title compound as a foam.

EXAMPLE 14

6'-(2-[Benzyloxycarbonylamino]-2-[4-acetoxyphenyl]acetamido)penicillanoyloxymethyl Penicillanate 1,1-Dioxide To a stirred solution of 2.23 g of 6'-(2-benzyloxycarbonylamino-2-[4-hydroxyphenyl]acetamido)penicillanoyloxymethyl penicillanate 1,1-dioxide in 50 ml of dichloromethane was added 0.28 ml of acetic anhydride followed by 0.366 g of 4-dimethylaminopyridine. Stirring was continued for 10 minutes and then the solvent was removed by evaporation in vacuo. The residue was dissovled in ethyl acetate, and the solution obtained was washed with water. It was then dried using sodium sulfate and concentrated in vacuo to give 2.0 g of the title compound as a foam.

The NMR spectrum (in CDCl₃) showed absorptions at 1.35–1.60 (m, 12H), 2.25 (s, 3H), 3.40 (d, 2H), 4.38 (s, 2H), 4.56 (t,1H), 5.04 (s, 2H), 5.20–5.60 (m, 3H), 5.80 (s, 2H), 6.12 (d, 1H), 6.48 (d, 2H), 7.24 (s, 5H) and 7.30 (d, 2H) ppm.

EXAMPLE 15

6'-(2-[4-Nitrobenzyloxycarbonylamino]-2-[4-toxy-phenyl]acetamido)penicillanoyloxymethyl Penicillanate 1,1-Dioxide By acetylation of 6'-(2-[4-nitrobenzyloxycarbonylamino]-2-[4-hydroxyphenyl]acetamido)penicillanoyloxymethyl penicillanate 1,1-dioxide with acetic anhydride, according to the procedure of Example 14, the title compound can be prepared.

EXAMPLE 16

6'-(2-Amino-2-[4-butyryloxyphenyl]acetamido)penicillanoyloxymethyl Penicillanate 1,1-Dioxide 4-Toluenesulfonate To a stirred solution of 7.1 g of 6'-(2-[1-methyl-2-methoxycarbonylvinylamino]-2-[4-hydroxyphenyl]acetamido)penicillanoyloxymethyl penicillanate 1,1-dioxide in 75 ml of ethyl acetate was added 1.22 g of 4-dimethylaminopyridine followed by 1.63 ml of butyric anhydride. Stirring was continued for 20 minutes and then the reaction medium was diluted with ethyl acetate to 125 ml and washed with water and with saturated sodium chloride solution. The solution obtained was dried using sodium sulfate, and then a solution of 1.9 g of 4-toluenesulfonic acid monohydrate in 35 ml of ethyl acetate and 1 ml of water was added, with stirring, during 2 minutes. After 30 minutes the precipitate was recovered by filtration, and then it was washed with ethyl acetate and air dried. The product was then triturated under diethyl ether and further dried. This afforded 6.2 g of the title compound.

The NMR spectrum of the product (DMSO-d$_6$) showed absorptions at 1.03 (t, 2H), 1.3–1.9 (m, 14H), 2.33 (s, 3H), 2.4–2.8 (m, 2H), 3.1–3.9 (m, 2H), 4.46 (s, 1H), 4.56 (s, 1H), 5.06–5.3 (m, 2H), 5.4–5.66 (m, 2H), 5.93 (bs, 2H), 7.0–7.36 (m, 4H) and 7.4–7.66 (m, 4H) ppm.

The IR spectrum of the product (nujol mull) showed an absorption at 1790 cm$^{-1}$.

EXAMPLE 17

Hydrogenolysis of the appropriate compound from Example 18, using the procedure of Example 4, affords the following compounds:

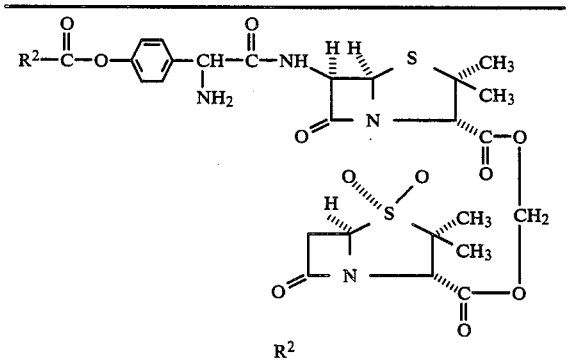

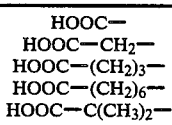

| R$^2$ |
|---|
| HOOC— |
| HOOC—CH$_2$— |
| HOOC—(CH$_2$)$_3$— |
| HOOC—(CH$_2$)$_6$— |
| HOOC—C(CH$_3$)$_2$— |

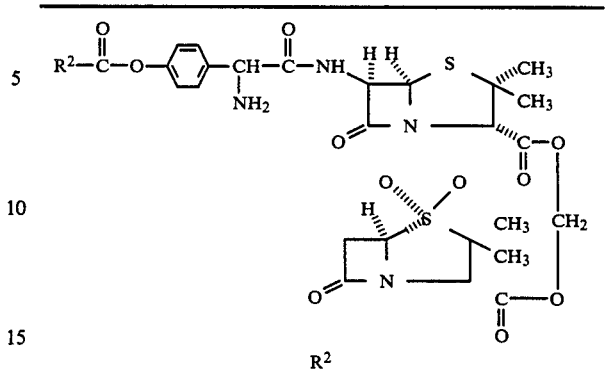

EXAMPLE 18

Acylation of 6'-(2-benzyloxycarbonylamino-2-[4-hydroxyphenyl]acetamido)penicillanoyloxymethyl penicillanate 1,1-dioxide with the appropriate acid chloride of the formula R$^7$—C(=O)—Cl, according to the procedure of Example 8, affords the following compounds:

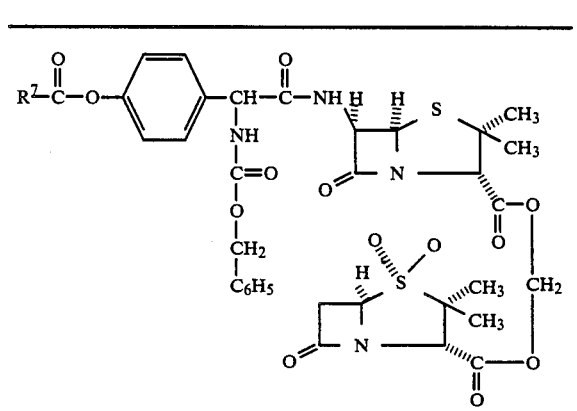

| R$^7$ |
|---|
| C$_6$H$_5$—CH$_2$—O—CO— |
| C$_6$H$_5$—CH$_2$—O—CO—CH$_2$— |
| C$_6$H$_5$—CH$_2$—O—CO(CH$_2$)$_3$— |
| C$_6$H$_5$—CH$_2$—O—CO(CH$_2$)$_6$— |
| C$_6$H$_5$—CH$_2$—O—CO—C(CH$_3$)$_2$— |

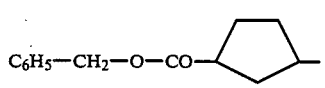

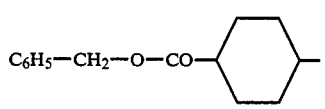

EXAMPLE 19

6'-(2-Amino-2-[4-(N-n-butylcarbamoy)oxylphenyl]acetamido)penicillanoyloxymethyl Penicillanate 1,1-Dioxide Hydrochloride

To a stirred solution of 1.2 g of 6'-(2-[1-methyl-2-methoxycarbonylvinylamino]-2-[4-(N-n-butylcarbamoyloxy)phenyl]acetamido)penicillanoyloxymethyl penicillanate 1,1-dioxide in 30 ml of acetone was added 15 ml of 0.1 N hydrochloric acid. Stirring was continued for 20 minutes and then the acetone was removed by evaporation in vacuo. The remaining aqueous phase was washed with diethyl ether and then it was lyophilized. This afforded 0.97 g of the title compound.

The NMR spectrum (DMSO-$d_6$) showed absorptions at 0.7–1.1 (m, 3H), 1.1–1.6 (m, 16H), 2.8–3.9 (m, 4H), 4.13 (s, 1H), 4.5 (s, 1H), 5.0–5.3 (m, 2H), 5.36–5.6 (m, 2H), 5.9 (bs, 2H), 7.1 (d, 2H), 7.53 (d, 2H), 7.8 (m, 1H), 8.6–9.3 (m, 3H) and 9.4 (d, 1H) ppm.

EXAMPLE 20

6'-(2-[1-Methyl-2-methoxycarbonylvinylamino]-2-[4-(N-n-butylcarbamoyloxy)phenyl]acetamido)-penicilanoyloxymethyl Penicillanate 1,1-Dioxide

A mixture of 7.1 g of 6'-(2-[1-methyl-2-methoxycarbonylvinylamino]-2-[4-hydroxyphenyl]acetamido)-penicillanoyloxymethyl penicillanate 1,1-dioxide, 1.46 g of 4-dimethylaminopyridine and 50 ml of dichloromethane was stirred until a clear solution was obtained. To this solution was added 2.2 ml of n-butyl isocyanate and stirring was continued for 20 minutes. The solvent was removed by evaporation in vacuo and the residue was chromatographed on 500 g of silica gel, eluting with 60:40 dichloromethane-ethyl acetate. The product containing fractions were combined and evaporated in vacuo to give 1.2 g of the title compound as a white foam.

The NMR spectrum (CDCl$_3$) showed absorptions at 0.7–1.1 (m, 3H), 1.2–1.65 (m, 16H), 3.6 (s, 3H), 4.4 (s, 2H), 4.5–4.7 (m, 2H), 5.1 (d, 1H), 5.3–5.65 (m, 2H), 5.9 (bs, 2H), 6.85 (d, 2H), 7.06 (m, 2H), 7.33 (d, 2H) and 9.4 (d, 2H) ppm.

EXAMPLE 21

By reaction of 6'-(2-[1-methyl-2-methoxycarbonylvinylamino]-2-[4-hydroxyphenyl]acetamido)penicillanoyloxymethyl penicillanate 1,1-dioxide with isopropyl isocyanate, phenyl isocyanate, 3-iodophenyl isocyanate and 4-chlorophenyl isocyanate, respectively, using the procedure of Example 20, followed by hydrolysis of each of the products obtained using the procedure of Example 19, the following compounds can be obtained:
6'-(2-amino-2-[4-(N-isopropylcarbamoyloxy)phenyl]acetamido)penicillanoyloxymethyl penicillanate 1,1-dioxide hydrochloride,
6'-(2-amino-2-[4-(N-phenylcarbamoyloxy)phenyl]acetamido)penicillanoyloxymethyl penicillanate 1,1-dioxide hydrochloride,
6'-(2-amino-2-[4-(N-[3-iodophenyl]carbamoyloxy)phenyl]acetamido)penicillanoyloxymethyl penicillanate 1,1-dioxide hydrochloride and
6'-(2-amino-2-[4-(N-[4-chlorophenyl]carbamoyloxy)phenyl]acetamido)penicillanoyloxymethyl penicillanate 1,1-dioxide hydrochloride, respectively.

PREPARATION 1

6'-(2-[1-Methyl-2-methoxycarbonylvinylamino]-2-[4-hydroxyphenyl]acetamido)penicillanoyloxymethyl Penicillanate 1,1-Dioxide

To 300 ml of dichloromethane was added 41.9 g of 6-(2-amino-2-[4-hydroxyphenyl]acetamido)penicillanic acid trihydrate and 50 ml of water, and then the pH was adjusted to 8.5 using 40% aqueous tetra-n-butylammonium hydroxide. Three layers were obtained. The upper layer was removed, saturated with sodium sulfate and then it was extracted with dichloromethane. The extracts were combined with the middle layer and the lower layer, and the resulting mixture was evaporated in vacuo to give an oil which crystallized on trituration with acetone. This afforded 44.6 g of tetra-n-butylammonium 6-(2-amino-2-[4-hydroxyphenyl]acetamido)-penicillanate.

The above salt was added to 150 ml of methyl acetoacetate and the suspension was heated at ca. 65° C. until a clear solution was obtained (8 minutes). The mixture was allowed to cool, and then the solid was recovered by filtration. The solid was washed with methyl acetoacetate, followed by diethyl ether, to give 49.25 g of tetra-n-butylammonium 6-(2-[1-methyl-2-methoxycarbonylvinylamino]-2-[4-hydroxyphenyl]acetamido)-penicillanate.

To 47.5 g of the latter product in 250 ml of dimethylformamide at 0° C. was added, with stirring, 18.26 g. of iodomethyl penicillanate 1,1-dioxide in 50 ml of the same solvent, over a 20 minute period. Ten minutes after completion of the addition, the reaction mixture was poured into 3 l. of ethyl acetate and the resulting precipitate was filtered off. The precipitate was washed with ethyl acetate (100 ml), and then the combined ethyl acetate solution was washed successively with a brine solution (4×500 ml), water (4×500 ml) and a brine solution (2×500 ml) and dried over sodium sulfate. The residue remaining after the solvent was removed was chromatographed over 750 g of silica gel using ethyl acetate as the eluant. The fractions (250 ml. each) 2–5 were combined and concentrated to give 31.2 g of the title compound.

The NMR spectrum (DMSO-$d_6$, $^1$H 100.1 M Hz) showed absorptions at 1.37 (s, 3H), 1.38 (s, 3H), 1.48 (s, 3H), 1.57 (s, 3H), 1.76 (s, 3H), 3.14–3.82 (m, 2H), 3.51 (s, 3H), 4.42 (s, 1H), 4.44 (s, 1H), 4.54 (s, 1H), 5.1–5.22 (m, 1H), 5.3–5.64 (m, 3H), 5.9 (s, 2H), 6.7 (d, 2H), 7.14 (d, 2H), 9.02 (d, 1H), 9.24 (d, 1H) and 9.34–9.54 (bs, 1H) ppm.

Repetition of the above procedure, but using an equimolar amount of ethyl acetoacetate and isopropyl acetoacetate, respectively, instead of the methyl acetoacetate, affords 6'-(2-[1-methyl-2-ethoxycarbonylvinylamino]-2-[4-hydroxyphenyl]acetamido)penicillanoyloxymethyl penicillanate 1,1-dioxide and 6'-(2-[1-methyl-2-isopropoxycarbonylvinylamino]-2-[4-hydroxyphenyl]acetamido)penicillanoyloxymethyl penicillanate 1,1-dioxide, respectively.

PREPARATION 2

6'-(2-Benzyloxycarbonylamino-2-[4-hydroxyphenyl]acetamido)penicillanoyloxymethyl Penicillanate 1,1-Dioxide

To 9.5 g of tetra-n-butylammonium 6-(2-benzyloxycarbonylamino-2-[4-hydroxyphenyl]acetamido)-penicillanate in 50 ml of dry acetone was added 4.78 g of iodomethyl penicillanate 1,1-dioxide, and the reaction mixture allowed to stir at room temperature for 30 min. The reaction mixture was concentrated in vacuo and the residue was chromatographed on 200 g. of silica gel using ethyl acetate/dichloromethane (1:1 v:v), 25 ml. cuts being made. Fractions 29-49 were combined and concentrated to give 6.5 g of the desired product as a yellow foam.

The NMR spectrum (DMSO-$d_6$) showed absorptions at 1.42 (s, 3H), 1.52 (s, 3H), 1.6 (s, 3H), 3.1-3.9 (m, 2H), 4.45 (s, 1H), 4.58 (s, 1H), 5.08 (s, 2H), 4.98$_{5.7}$ (m, 4H), 5.95 (s, 2H), 6.68 (d, 2H), 7.2 (d, 2H) and 7.35 (s, 5H) ppm.

PREPARATION 3

6'-(2-[4-Nitrobenzyloxycarbonylamino]-2[4-hydroxyphenyl]acetamido)penicillanoyloxymethyl Penicillanate 1,1-Dioxide By reaction of tetra-n-butylammonium 6-(2-[4-nitrobenzyloxycarbonylamino]-2-[4-hydroxyphenyl]acetamido)penicillanate with iodomethyl penicillanate 1,1-dioxide, according to the procedure of Preparation 2, the title compound can be prepared.

PREPARATION 4

Tetra-n-butylammonium 6-(2-Benzyloxycarbonylamino-2-[4-hydroxyphenyl]acetamido)penicillanate To a rapidly stirred mixture of 1.0 g of 6-(2-benzyloxycarbonylamino-2-[4-hydroxyphenyl]acetamido)penicillanic acid, 30 ml of dichloromethane and 20 ml of water was added 40% aqueous tetra-n-butylammonium hydroxide until a pH of 8.0 was obtained. Stirring was continued for 30 minutes at pH 8.0 and then the layers were separated. The aqueous layer was extracted with dichloromethane, and then the combined dichloromethane solutions were dried ($Na_2SO_4$) and evaporated in vacuo. This afforded 1.1 g of the title compound.

The NMR spectrum (in DMSO-$d_6$) showed absorptions at 0.70-1.80 (m, 34H), 2.90-3.50 (m, 8H), 3.93 (s, 1H), 5.10 (s, 2H), 5.23-5.50 (m, 3H), 6.76 (d, 2H), 7.20 (d, 2H), 7.40 (s, 5H), 7.76 (d, 1H) and 8.6 (d, 1H) ppm.

PREPARATION 5

Tetra-n-butylammonium 6-(2-[4-Nitrobenzyloxycarbonylamino]-2-[4-hydroxyphenyl]acetamido)penicillanate The title compound can be obtained from 6-(2-[4-nitrobenzyloxycarbonylamino]-2-[4-hydroxyphenyl]acetamido)penicillanic acid and tetra-n-butylammonium hydroxide, using the procedure of Preparation 4.

PREPARATION 6

Chloromethyl Penicillanate 1,1-Dioxide

A mixture of 4.66 g of penicillanic acid 1,1-dioxide, 50 ml of dichloromethane and 35 ml of water was treated with sufficient tetra-n-butylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetra-n-butylammonium salt of penicillanic acid 1,1-dioxide.

The above tetra-n-butylammonium penicillanate 1,1-dioxide was added to 50 ml of chloroiodomethane and the reaction mixture allowed to stir at ambient temperature overnight. The reaction mixture was concentrated to half volume in vacuo, and chromatographed on 200 g of silica gel using ethyl acetate/hexane as the eluant, 12 ml cuts being taken every 30 seconds. Fractions 41-73 were combined and concentrated to dryness to give 3.2 g of the title compound.

The NMR spectrum ($CDCl_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION 7

Iodomethyl Penicillanate 1,1-Dioxide

To a solution of 7.9 g of chloromethyl penicillanate 1,1-dioxide in 100 ml of dry acetone maintained under a nitrogen atmosphere was added 21.0 g of sodium iodide, and the reaction mixture was allowed to stir overnight at room temperature. The reaction mixture was concentrated in vacuo, and the residue was dissolved in 150 ml ethyl acetate and 150 ml water. The organic layer was separated and the aqueous layer was extracted with fresh ethyl acetate. The organic extracts were combined, washed with water (1×500 ml) and brine (1×50 ml) and dried over sodium sulfate. Removal of the solvent gave 10.5 g of the title product, m.p. 100°-102° C.

The NMR spectrum ($CDCl_3$) showed absorptions at 1.55 (s, 3H), 1.68 (s, 3H), 3.5 (d, 2H), 4.4 (s, 1H), 4.65 (t, 1H) and 6.0 (dd, 2H) ppm.

PREPARATION 8

Mono Benzyl Ester Mono Acid Chloride of Dimethylmalonic Acid

A mixture of 1.0 g of the mono benzyl ester of dimethylmalonic acid, 1.0 ml of thionyl chloride and 15 ml of dichloromethane is stirred at room temperature for 1 hour and then it is heated under reflux for 4 hours. The volatile components are then removed by evaporation in vacuo to afford the title compound, which is used directly to acylate a compound of formula X.

PREPARATION 9

Reaction of the mono benzyl ester of the appropriate dicarboxylic acid with thionyl chloride, using the procedure of Preparation 8, affords the following acid chlorides:

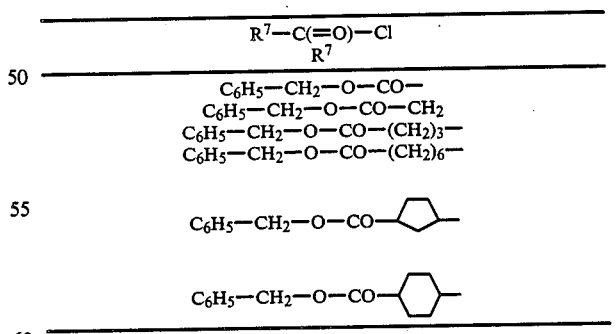

PREPARATION 10

Mono Benzyl Ester of Dimethylmalonic Acid

A solution of 3.12 g (4.8 mmole) of 85% potassium hydroxide in 75 ml benzyl alcohol was added to 15.0 g dibenzyl dimethylmalonate in 75 ml benzyl alcohol. The resulting solution was stirred for 60 hours, 1.5 liters of ethyl ether added and the resulting mixture extracted twice with 100 ml portions of water. The combined aqueous layers were washed with 100 ml ether. To the aqueous layer was added 100 ml ethyl ether and the mixture was acidified to pH 2.5 with 6N hydrochloric acid. The ether layer was separated and the aqueous phase extracted again with ether. The ether extracts were dried ($Na_2SO_4$) and solvent evaporated to afford the product as a colorless oil, 8.6 g (81%).

Using the above procedure can be prepared the following mono benzyl esters:

| $R^7$ | $R^7-C(=O)-OH$ |
|---|---|
| $C_6H_5-CH_2-O-CO-$ | |
| $C_6H_5-CH_2-O-CO-CH_2-$ | |
| $C_6H_5-CH_2-O-CO-(CH_2)_3-$ | |
| $C_6H_5-CH_2-O-CO-(CH_2)_6-$ | |
| $C_6H_5-CH_2-O-CO-\langle cyclopentyl \rangle$ | |
| $C_6H_5-CH_2-O-CO-\langle cyclohexyl \rangle$ | |

PREPARATION 11

Dibenzyl Dimethylmalonate

To 75 ml water containing 4.0 g sodium hydroxide was added at 0° C., 17.0 g (0.05 mole) tetrabutylammonium hydrogen sulfate, the mixture was stirred 15 minutes, allowed to warm and 100 ml chloroform containing 14.2 g (0.05 mole) dibenzyl malonate and 6.6 ml (0.10 mole) methyl iodide was added. The mixture (initial pH >12) was stirred for 30 minutes at which time the mixture was pH ca. 8. Stirring was continued for ten minutes, the organic phase was separated. To the organic layer was added another charge of 4.0 g sodium hydroxide, 17.0 g tetrabutylammonium hydrogen sulfate in 75 ml water and 6.6 g methyl iodide. The resulting mixture was stirred at room temperature for 30 minutes, the chloroform layer was separated, dried ($Na_2SO_4$) and concentrated in vacuo. The resulting residual oil was triturated with 500 ml ethyl ether, the resulting solids were filtered, washed well with ether and the filtrate and washings evaporated to afford 15.0 g (96%) of product.

I claim:

1. A compound of the formula

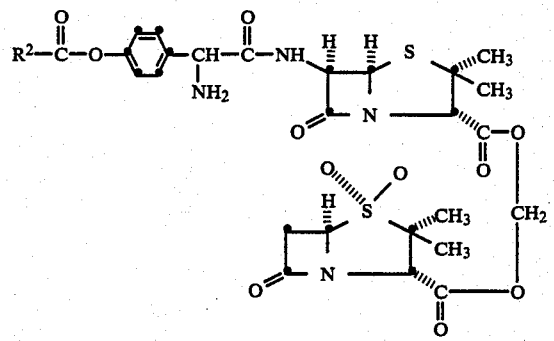

the pharmaceutically-acceptable acid addition salts thereof and the pharmaceutically-acceptable base salts thereof;
wherein $R^2$ is alkyl having from one to six carbons.
2. The compound according to claim 1, wherein $R^2$ is isopropyl.
3. A pharmaceutical composition, suitable for treating a bacterial infection in a mammalian subject, which comprises an antibacterially effective amount of a compound according to claim 1 and a pharmaceutically-acceptable carrier.
4. A method of treating a bacterial infection in a mammalian subject, which comprises administering thereto an antibacterially effective amount of a compound of the formula

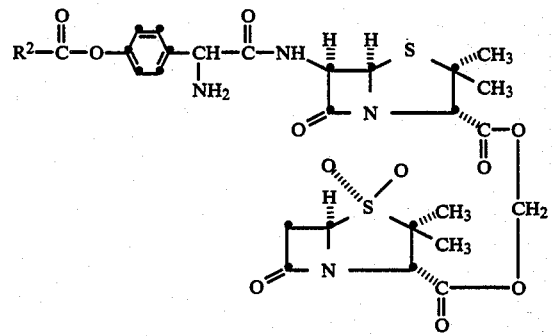

or a pharmaceutically-acceptable acid addition salt thereof or a pharmaceutically-acceptable base salt thereof;
wherein $R^2$ is alkyl having from one to six carbons.
5. The method according to claim 4, wherein $R^2$ is isopropyl.
6. A compound of the formula

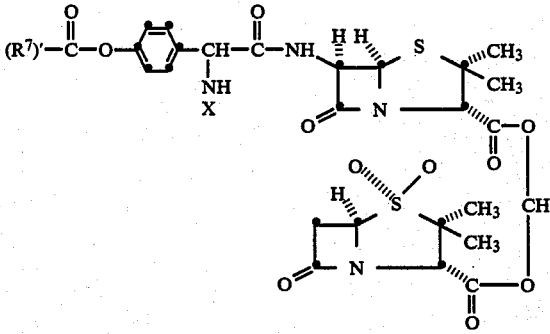

wherein X is selected from the group consisting of 1-methyl-2-alkoxycarbonylvinyl having 1 to 3 carbons in said alkoxy moiety, benzyloxycarbonyl and 4-nitrobenzyloxycarbonyl;
and $(R^7)'$ is alkyl having from one to six carbons.
7. A compound according to claim 6, wherein X is 1-methyl-2-methoxycarbonylvinyl.
8. The compound according to claim 7, wherein $(R^7)'$ is isopropyl.

* * * * *